US008585774B2

(12) United States Patent
Henderson

(10) Patent No.: US 8,585,774 B2
(45) Date of Patent: Nov. 19, 2013

(54) TEMPORAL BROW LIFTING AND FIXATION DEVICE

(76) Inventor: Jenifer Lee Henderson, Bainbridge Island, WA (US)

(*) Notice: Subject to any disclaimer, the term of this patent is extended or adjusted under 35 U.S.C. 154(b) by 39 days.

(21) Appl. No.: 13/285,709

(22) Filed: Oct. 31, 2011

(65) Prior Publication Data

US 2012/0046759 A1 Feb. 23, 2012

Related U.S. Application Data

(62) Division of application No. 11/675,612, filed on Feb. 15, 2007, now abandoned.

(51) Int. Cl.
*A61F 2/02* (2006.01)

(52) U.S. Cl.
USPC ............ 623/23.72; 623/23.75; 606/215

(58) Field of Classification Search
USPC ......... 623/23.72, 23.74, 23.75; 606/153, 154, 606/155, 213, 215, 216, 221, 204.35
See application file for complete search history.

(56) References Cited

U.S. PATENT DOCUMENTS

| | | | |
|---|---|---|---|
| 3,981,051 A | 9/1976 | Brumlik | |
| 4,259,959 A | 4/1981 | Walker | |
| 4,430,998 A | 2/1984 | Harvey | |
| 4,548,202 A | 10/1985 | Duncan | |
| 5,139,497 A * | 8/1992 | Tilghman et al. | 606/285 |
| 5,217,494 A * | 6/1993 | Coggins et al. | 623/23.72 |
| 5,254,127 A | 10/1993 | Wholey | |
| 5,383,897 A | 1/1995 | Wholey | |
| 5,916,224 A | 6/1999 | Esplin | |
| 5,925,078 A | 7/1999 | Anderson | |
| 6,241,747 B1 | 6/2001 | Ruff | |
| 6,328,743 B2 | 12/2001 | Lerch | |
| 6,485,503 B2 | 11/2002 | Jacobs | |
| 6,645,226 B1 | 11/2003 | Jacobs | |
| 6,893,452 B2 | 5/2005 | Jacobs | |
| 6,991,643 B2 | 1/2006 | Saadat | |
| 7,056,331 B2 * | 6/2006 | Kaplan et al. | 606/228 |
| 7,510,566 B2 | 3/2009 | Jacobs | |
| 2001/0044637 A1 | 11/2001 | Jacobs | |
| 2002/0022861 A1 | 2/2002 | Jacobs | |
| 2002/0173807 A1 | 11/2002 | Jacobs | |
| 2002/0198544 A1 * | 12/2002 | Uflacker | 606/144 |
| 2003/0065360 A1 | 4/2003 | Jacobs | |

(Continued)

OTHER PUBLICATIONS

Mutaf, M., "Mesh Lift: A New Procedure for Long-Lasting Results in Brow Lift Surgery", Plastic Reconstructive Surgery (2005), 116(5), 1490-1499.*

*Primary Examiner* — Corrine M McDermott
*Assistant Examiner* — Jing Ou
(74) *Attorney, Agent, or Firm* — Christensen O'Connor Johnson Kindness PLLC

(57) ABSTRACT

The present invention describes an implantable tissue lifting and fixation device. More particularly, the present invention describes a temporal brow lifting device comprised of a bioabsorbable supportive backing. The device has a shape of a curvilinear end and a tail end region. The curvilinear end region comprises a plurality of attachment points protruding from the supportive backing, and the tail region comprises of a plurality of cavities in order to secure the device at the desired elevated position in the deep temporal fascia. The plurality of attachment points distributes tension in a multi-vector direction over the contact area between the device and the tissue. The attachment points can be manufactured separately and attached, however, preferably, the attachment points are made integral with the temporal brow lifting device.

18 Claims, 12 Drawing Sheets

(56) References Cited

U.S. PATENT DOCUMENTS

| | | |
|---|---|---|
| 2003/0069602 A1 | 4/2003 | Jacobs |
| 2003/0074021 A1 | 4/2003 | Morriss |
| 2004/0010275 A1 | 1/2004 | Jacobs |
| 2004/0010276 A1 | 1/2004 | Jacobs |
| 2005/0118388 A1 | 6/2005 | Kingsford |
| 2005/0119694 A1 | 6/2005 | Jacobs |
| 2005/0197699 A1 | 9/2005 | Jacobs |
| 2009/0082791 A1* | 3/2009 | Schroeder et al. ............ 606/151 |

* cited by examiner

TEMPORAL BROW LIFTING AND FIXATION DEVICE

CROSS-REFERENCE TO RELATED APPLICATION

This application is a division of U.S. patent application Ser. No. 11/675,612, now abandoned filed Feb. 15, 2007, which is expressly incorporated herein by reference.

BACKGROUND OF THE INVENTION

The present invention relates to an implantable tissue lifting and fixation device. More particularly, the present invention relates to a temporal brow lifting device, which is used to lift and fix the brows at an elevated position in a brow lifting surgery and similar surgical procedures. The temporal brow lifting device of the present invention is comprised of a bio-resorbable supportive backing having a curvilinear end region and a tail end region. The curvilinear end region comprises a plurality of attachment points to facilitate brow-lift, and the tail end region having a plurality of cavities to secure the device at the desired position.

The brow lift is a basic procedure for rejuvenating the upper portion of a patient's face. The brow lift procedure may be used to elevate the eyebrows, remove or lessen forehead wrinkles, reduce frown lines, smooth the nasion and elevate the nasal tip. Various surgical approaches are available for the brow lift, including the direct brow lift, mid forehead lift, pretrichial lift, temporal lift, coronal lift, and endoscopic lift.

In carrying out the brow lift surgery, once the surgeon has moved the brow to a superior position, the soft tissue must be suspended in that position for a sufficient time to allow healing to occur. Conventionally, external means, such as screws and staples, have been used to suspend the soft tissue in place. These devices may leave the patient susceptible to infections, require a great deal of bandaging, and leave extensive scars. Internal means, such as surgical pins or posts, also have been applied however these devices require the surgeon to reopen the skin to remove them. Further, tissue fixation methods that do not a require reopening of the patient's skin to remove fixation devices have been attempted, such as deployment of resorbable fixation devices. An ideal resorbable fixation device should have the ability to adjust the timing for the release of the fixation device after implantation in response to individual healing rates.

The temporal brow lift also known as lateral lift or lateral brow lift is a more lateral-diagonal lift. The temporal lift can relieve folds and small wrinkles in the forehead and can also lift the cheek skin. Therefore, it is desirable to use a temporal brow lifting procedure in combination with a bio-resorbable implant to achieve the desired brow lifting effects.

U.S. Pat. No. 5,611,814, issued to Lorenc, describes a resorbable surgical appliance for a mid-forehead brow lifting surgical procedure in order to support soft tissue at a superior position. Lorenc describes the surgical appliance is comprised of a coupling member that connects the surgical appliance to the bone or hard tissue and a gripping member(s) to grip or retain the soft tissue at the superior position. However, the head of such screws or tacks and the gripping member of such appliances are bulky, making a prominent protrusion on the bone surface. Moreover, the surgical procedure requires drilling of the surgical appliance in the bone or skull of the patient.

U.S. Pat. No. 6,015,410, issued to T. Pertti, et al., describes a bioabsorbable surgical implant for use in mid-forehead brow lifting procedure, to support soft tissue at a superior position in the body. The surgical implant includes a shaft that connects the implant to a bone or hard tissue and a head secured to the shaft. The head of the implant has a concave lower surface so that a suture (or sutures) can easily be wound around the shaft below the head and locked to this position by tightening the head against bone or hard tissue and by pushing or turning the shaft into the bone or hard tissue.

U.S. Pat. No. 6,485,503, issued to J. Daniel, et al., describes an implantable tissue approximation device for mid-forehead brow lifting surgical procedure. The device comprises of attachment points and a post in order to secure the device into the cranium of the patient. The scalp tissue to be lifted may be set on a brow lift device via attachment points, and the device may then be secured to a patient's cranium. The brow lifting device requires drilling of skull or cranium in order to secure the device.

Conventionally, suture fixation is used in order to secure the temporal brow in an elevated position following temporal brow-plasty. Suture fixation, generally, provides a single vector of pull which can result in an unnatural, tented appearance to the temporal brow. Moreover, suture fixation can be cumbersome and may require several attempts by the surgeon to achieve bilateral symmetry.

Therefore, there is a need to develop a low profile, bio-resorbable tissue lifting and fixation device to be used in a temporal brow lifting surgery and similar surgical procedures. Further, there is a need to develop a tissue lifting and fixation device that can generate a multi-vector pull on a tissue to achieve a better cosmetic appearance.

SUMMARY OF THE INVENTION

It is the objective of the present invention to provide an implantable device for a temporal brow lift surgery and similar surgical procedure.

Another objective of the invention is to provide a bio-resorbable implant for a temporal brow lifting surgery and similar surgical procedure.

A further objective of the present invention is to provide a low profile implant for a temporal brow lifting surgery and similar surgical procedure To achieve the aforementioned objectives, the present invention discloses an implantable tissue lifting and fixation device to be used for a temporal brow lifting surgery and similar surgical procedure. The device of the present invention comprises of a supportive backing having a proximal surface, directly in contact with the patient's body, and a distal surface. Further the device periphery consists of a curvilinear end region and a tail region. The curvilinear region comprising a plurality of attachment points protruding from the supportive backing, and the tail region is provided with a plurality of cavities to secure the device by suturing at the desired position into the deep temporal fascia the proximal surface has no attachment points.

In an embodiment of the present invention, the temporal brow lifting device comprises of a supportive backing. The supportive backing has a shape of a curvilinear first end and a tail end region. The curvilinear end region comprises of a plurality of attachment points protruding from the supportive backing. The attachment point distributes tension over the contact area between the temporal brow lifting device and the tissue.

The shape and size of the curvilinear end region can vary depending upon the usage. The curvilinear region is configured to position the device at the lateral orbital rim of the brow of a user. In the brow lifting device, preferably used for the male user, the curvilinear region is provided with a lateral length of 40 mm. Similarly, for the female user, the curvilinear region has a lateral length of 30 mm.

The attachment points can be canted or erect shape. Furthermore, the tip of the attachment points may be varied. The position of the individual attachment points and their density on the supportive backing can vary depending on the type and ease for securing tissue to attachment points and on the distribution of loads generated by the attached tissue over each of the attachment points. The attachment points can be manufactured separately and attached, however, preferably the attachment points are made integral with the temporal brow lifting device.

The supportive backing material might be produced from a more flexible polymer and the attachment points or tines of a stiffer material. The supportive backing, generally, is made of a bio-resorbable material that can have the structure of a mesh, net, or lattice. The extent of porosity or total surface area may be used to control the absorption rate of the device, and may also be used to optimize the strength-to-mass properties of the device, increasing the section modulus of structural cross-sections per unit mass. The backing structure may comprise partial folds, waves, or grooves to help hold tissue against both surfaces of the backing.

Materials such as biodegradable polymers are preferably used to construct the backing and attachment points. Examples of biodegradable polymers are polyglycolide, polylactide, poly-α-caprolactone, polydiaxanone, polyglyconate, polylactide-co-glycolide, and block and random copolymers of these polymers. An example of an inventive device may be made of two or more types of polymers or copolymers (or molecular weights of the same polymer or copolymer). Preferably, the bio-resorbable material used to construct the device of the present invention is a product marketed by Biomet, Inc. (Warsaw, Ind.), under the trademark LACTOSORB®. LACTOSORB®is an absorbable co-polymer synthesized from all natural ingredients: 82 percent L-lactic acid and 18 percent glycolic acid.

Further, the tissue implant device according to an embodiment of the present invention is described to be used in carrying out the temporal brow lift surgery. The device is designed to place against the brow in a low profile while secured to the fascia to provide a brow lift. The temporal brow lifting device is comprised of a curvilinear end region and a tail end region having a plurality of cavities. The tail extends from the mid-regions of the device and consists of cavities which can be used to secure the temporal brow in the desired elevated position. The temporal brow lifting device is inserted under a patient's brow while securely interlocking a small portion of the brow to the device preferably via a plurality of attachment points. After dissection of the lateral orbital rim of brow, the temporoparietal fascia is raised over the attachment points to lift the brow. The temporal brow lifting device can be secured into the deep temporal fascia by suturing it through the cavities of the tail region.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1A:
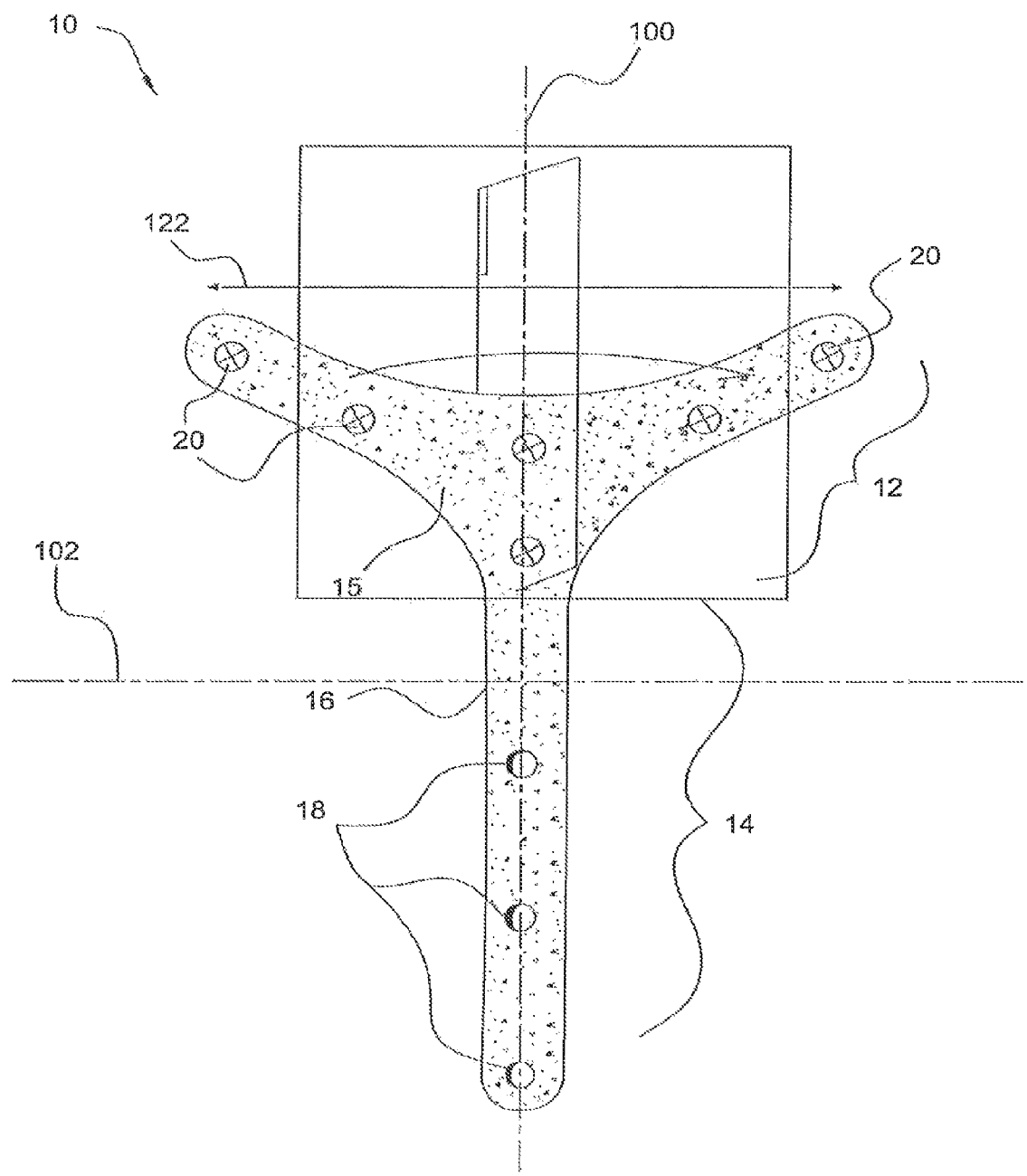
FIG. 1A shows a top view of a temporal brow lifting device of the present invention.

As used herein, the terms "temporal brow lifting device", "brow lifting device", or simply "fixation device" refer to an implantable tissue fixation device used in the brow lift surgery or similar surgical procedures. More specifically, these terms refer to a device that maintains the elevation of the brow after surgical dissection is complete. The device will hold the tissue until healing or scar formation is complete. A non-exhaustive list of brow lifting surgical procedures includes direct brow lift, mid forehead lift, pretrichial lift, trichophyte lift, temporal lift, coronal lift, and endoscopic brow lift.

As used herein, the terms "tines" or "prongs" both refer to the attachment points which are either sharp, i.e., able to separate tissue in a chosen use, or blunt, i.e., not able to separate tissue in that use. The attachment points may also be referred to as "barbs." Generally, the tines, prongs, or barbs penetrate into soft tissue and for a short distance. The attachment points preferably do not traumatize tissue in any major way, e.g., by penetration through a selected area of tissue to meet another device on the opposite side of the tissue.

Tangential Force as used herein refers to a force component that acts at a parallel direction to the surface at a given point.

Normal Force as used herein refers to a force that acts at perpendicular direction to the surface at a given point.

The term "longitudinal", as used herein, refers to an axis or direction in the plane of a device that is generally aligned with a vertical plane, which bisects the device into symmetrical left and right halves.

The term "lateral" refers to the line, axis, or direction perpendicular to the longitudinal direction, which lies within the plane of the device. The length in the longitudinal axis and lateral axis, respectively, represent the length and width of a device.

The present invention may be used with all of the foregoing classes of brow lift surgical procedures. The tissue fixation device of the present invention is a temporal brow lifting and fixation device. In the embodiments described herein provides as an exemplary structure of a brow lifting device to be used for the temporal brow lift surgical procedure, however this is not intended to limit the claimed invention.

The present invention discloses an implantable tissue lifting and fixation device. More particularly, the present invention relates to a temporal brow lifting device, used to lift the brow and similar surgical procedures. The temporal brow lifting device of the present invention comprises a bio-resorbable supportive backing having a curvilinear region and a tail end region.

The inventive device is specifically used for the temporal brow-lift surgical procedure. The curvilinear region of the device is configured to position the device at the lateral orbital rim of the brow. The curvilinear region comprises a plurality of attachment points protruding in a direction perpendicular to plane of the device. The plurality of the attachment points provides a multi-vector pull to the brow at an elevation position. The tail end region comprises a plurality of cavities. The cavities present at the tail end region are used to secure the device at the desired position by suturing. The length of the tail region can be varied depending upon the desired use.

The invention also relates to a method of performing a brow lift surgery using the inventive device. The method includes setting brow tissue layer onto the plurality of the attachment points. The method also includes mobilizing the lateral brow, securing the device to the temporal fascia (TPF), and suturing it to the deep temporal fascia of the patient through cavities present in the tail region.

The present invention will now be described with reference to the accompanying drawings. The drawings are being used to illustrate the inventive concept and do not intend to limit the invention to the embodiments shown in them. The brow lifting device of the present invention will be described. More particularly, the present invention describes a device, which can be used for a temporal brow lift surgery of both male and female individuals. It is understood that the device of the present invention can be equally adaptable to be used in other types of tissue lifting surgical procedures.

Referring to FIG. 1A, a top view of a tissue lifting device 10 according to an exemplary embodiment of the present invention is represented. The device 10 has a longitudinal axis 100 and a lateral axis 102 extends, respectively, along the length and width of the device. The device 10 has a front curvilinear region 12, and a longitudinal opposed tail end region 14. The embodiment shown in FIG. 1 is a temporal brow lifting device; however, this depiction is not intended to limit the invention.

Figure 1B:
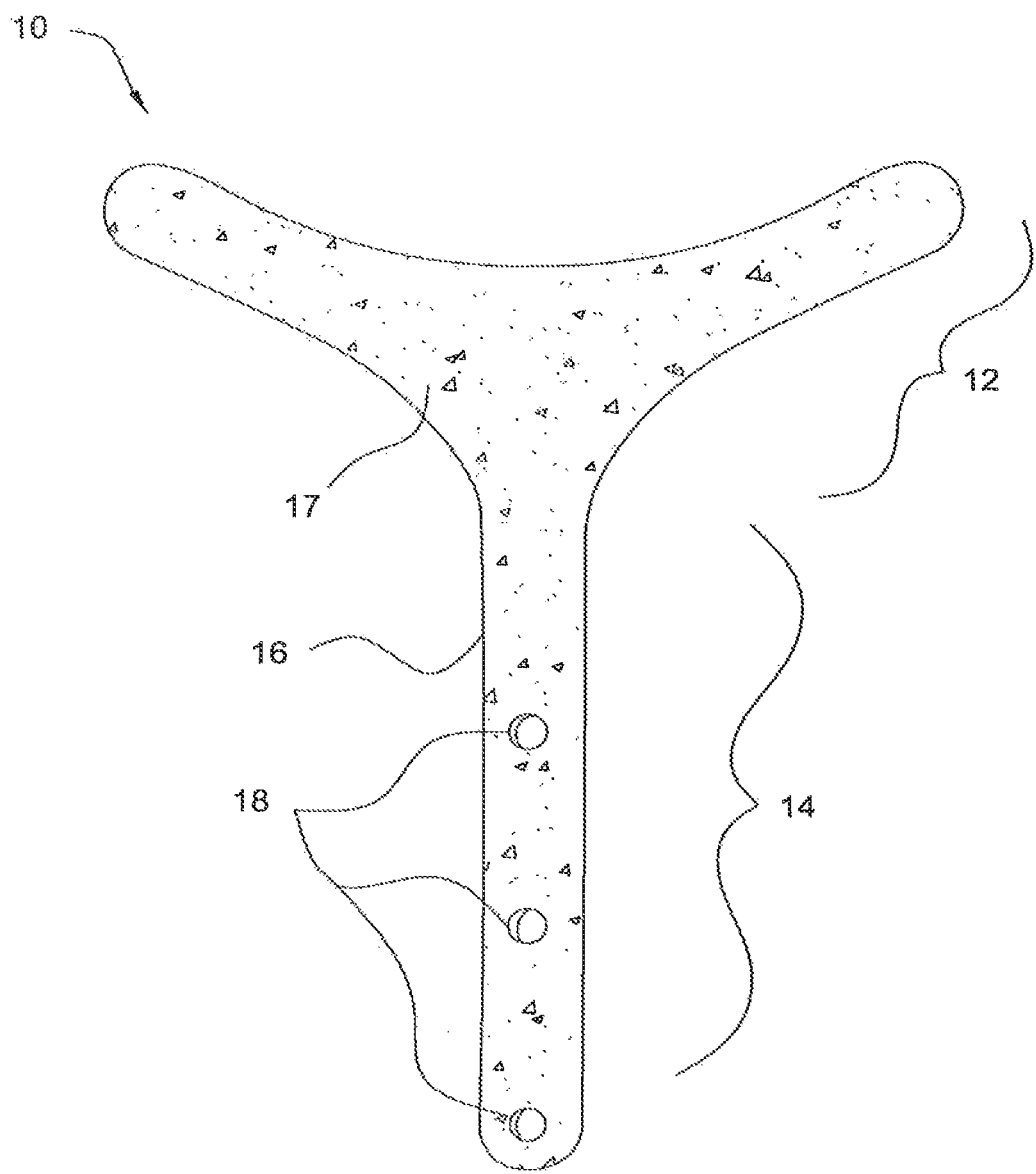
FIG. 1B shows a bottom view of the temporal brow lifting device of FIG. 1A.

The temporal brow lifting device 10, shown in FIG. 1, has a curvilinear end region 12, and a tail end region 14. The curvilinear end region 12 of the temporal brow lifting device 10 comprises a plurality of attachment points 20 protruding from and preferably affixed to a supportive backing 16. Preferably, the attachment points 20 are provided on the top surface, while the bottom surface, as shown in FIG. 1B, is planer and devoid of an attachment point. The tail end region 14 is provided with a plurality of cavities 18, so as to secure the device by suturing it at the desired temporal position of the patient's fascia.

The shape and size of the curvilinear region 12 varies depending upon the type and mode of usage. The curvilinear region 12 is configured to position the device onto the brow's lateral orbital rim of the user. Generally, male brows are parallel to the orbital rim or slightly lower, while female brows are higher in position than a male brow, and lay parallel to or above the level of the rim. The temporal brow lifting design for male has a longer curvilinear region while the female design is slightly smaller. In an embodiment, a temporal brow lifting device, preferably used for the male user, is provided with a curvilinear region having a lateral length, as shown in FIG. 1A as 122, of 40 mm. In another embodiment, a temporal brow lifting device, preferably used for the female user, is provided with a curvilinear region having a lateral length of 30 mm. Alternatively, variations in size of the curvilinear region of the temporal brow lifting device can be made and are within the scope of the present invention.

The supportive backing 16, generally, is made of a bio-resorbable material that can have the structure of a mesh, net, or lattice. The extent of porosity or total surface area may be used to control the absorption rate of the device and may also be used to optimize the strength-to-mass properties of the device, increasing the section modulus of structural cross-sections per unit mass. The backing structure may comprise partial folds, waves, or grooves to help hold tissue against both surfaces of the backing.

Materials such as biodegradable polymers are preferably used to construct the backing and attachment points. Polymers synthesized from monomers comprising esters, anhydrides, orthoesters, and amides are particularly suitable for biodegradation. Examples of biodegradable polymers are polyglycolide, polylactide, poly-α-caprolactone, polydiaxanone, polyglyconate, polylactide-co-glycolide, and block and random copolymers of these polymers. Preferably, copolymers of glycolic, lactic, and other α-hydroxy acids are highly desirable. The inflammatory response to these polymers is minimal, and they have been safely used in suture materials, stents, drug delivery devices, orthopedic fixation devices, and intestinal anastomotic rings. An example of an inventive device may be made of two or more types of polymers or copolymers (or molecular weights of the same polymer or copolymer). For instance, the backing material might be produced from a more flexible polymer and the points or tines of a stiffer material.

One resorbable material used in the inventive device is products marketed by Biomet, Inc. (Warsaw, Ind.) under the trademark LACTOSORB®. LACTOSORB® is an absorbable co-polymer synthesized from all natural ingredients: 82 percent L-lactic acid and 18 percent glycolic acid. Unlike the homopolymers in common use, such as 100 percent poly-L-lactic acid (PLLA) or 100 percent poly-glycolic acid (PGA), LACTOSORB® co-polymer is substantially amorphous (i.e., without crystallinity), meaning that its degradation is uniform, precluding the crystalline release most often associated with degrading homopolymers that have been associated with inflammatory reactions. Furthermore, the LACTOSORB® co-polymer ratio permits the polymer to retain most of its strength for six to eight weeks, which is appropriate for healing, but not so long as to raise concerns about long-term stress shielding. It should also be understood that any other type of resorbable material may also be used herein.

Figure 2A:
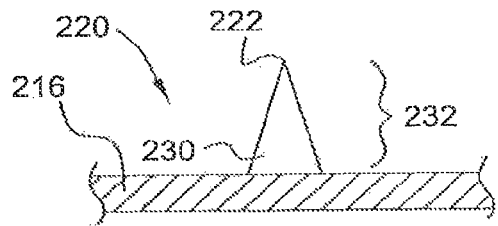
FIGS. 2A-2E represent side views of variations in the shapes and orientations of an attachment point, according to the present invention.
Figure 2D:
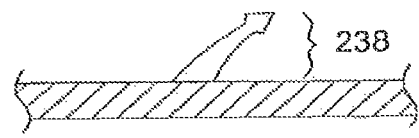
Figure 2B:
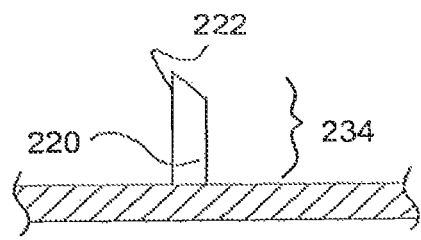
Figure 2E:
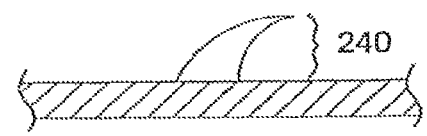
Figure 2C:
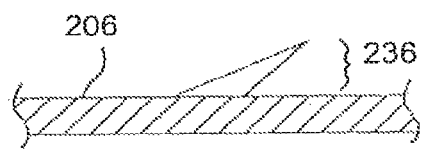
Figure 3A:
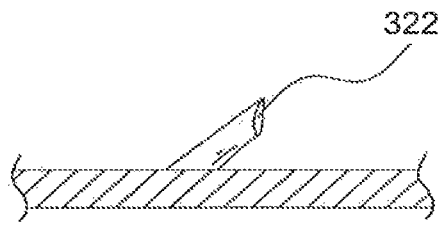
FIGS. 3A-3C represent perspective views of variations in the shapes of a tip of an attachment point, according to the present invention.
Figure 3B:
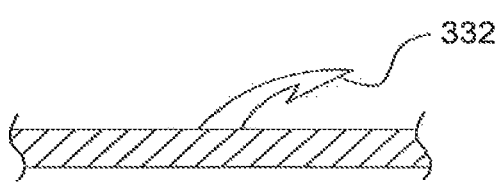
Figure 3C:
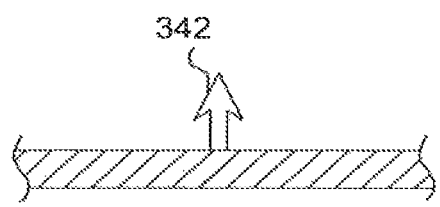

The shape of the attachment points 20 or tines can be varied depending, e.g., on the area of the body involved and the type of tissue requiring closure or re-approximation. Referring to FIGS. 2A-2E, various shape of the attachment points or tines are represented. As shown in FIG. 2A, the tines 220 have a wide base 230 that supports a projection 222 against the degree of tension required to close a wound or approximate tissue. For example, the attachment points can be erect tines as shown in FIG. 2A-232 and FIG. 2B-234, canted tines (FIG. 2C-236), canted arrowheads (FIG. 2D-238), canted hooks (FIG. 2E-240), or may have a shape configured to create a tangential force. Furthermore, the tip of the attachment points can be varied, as shown in FIGS. 3A-3C. The tips can be barbed, as shown in FIG. 3A-300, arrowhead (double-barb), shown in FIG. 3B as 302, or a faceted tip, shown in FIG. 3C as 304. The faceted tip is preferably desired when the force to penetrate tissue is normal to the tissue surface.

The connection of the attachment point or tine or prong to the backing may be rounded or filleted, or the backing built-up around the prong, to reduce structural stress concentrations. All edges of the device may be smooth except where sharpness is needed at the tip of the prong to pierce into the tissue. Once the prongs pierce into the tissue, the tissue may become supported against the backing to minimize additional piercing or irritation by the prong tip. The device may be molded, stamped, machined, woven, bent, welded, or otherwise fabricated to create the desired features and functional properties.

Figure 4A:
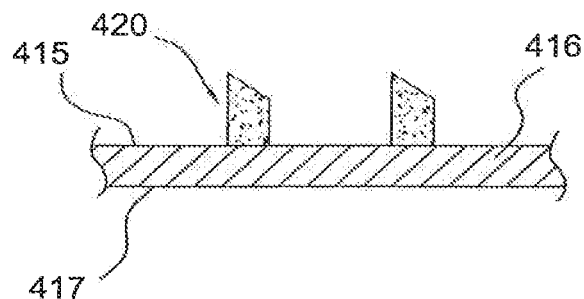
FIG. 4A shows a side, cross-sectional view of attachment points that run through the width of a supportive backing, according to the present invention.
Figure 4B:
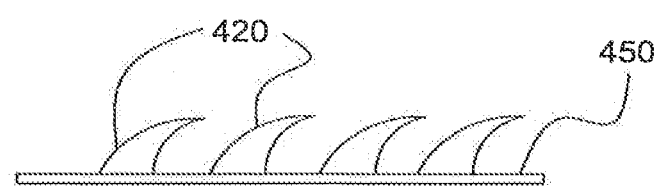
FIG. 4B shows a side view of attachment points on a strip of supportive backing material.
Figure 4C:
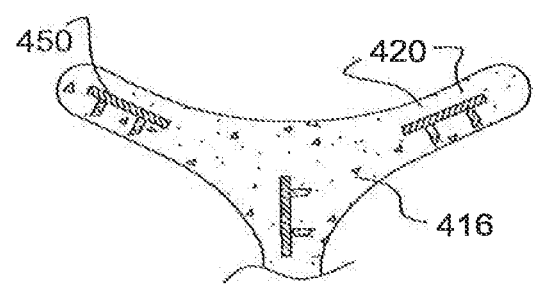
FIG. 4C is a plan, perspective view of the embodiment of FIG. 4B on a porous supportive backing.
Figure 4D:
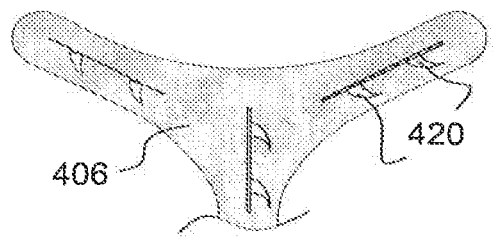
FIG. 4D shows a plan, perspective view of a solid supportive backing having a plurality of attachment points.

Structural variations can also be made to the supportive backing of the device. As shown in FIG. 4A, the attachment points 420 can be integral and protruding outward from the plane to the supportive backing. Alternatively, as shown in FIGS. 4B and 4C, the attachment points 420 may also connect to strips 450 of the same material as the attachment points which are then secured to a supportive backing 416. Further, as shown in FIG. 4D, the supportive backing may also be comprised of a solid material 406 instead of a porous material.

The attachment points 20 are provided with a shape of erected tines and are perpendicular to the plane of the supportive backing. Alternatively, the attachment points can be provided as projections having an angle elevation, towards the tail end region of the device. Further, position of the individual attachment point on the supportive backing can vary. However, the attachment points are placed in density so as to be optimally spaced relative to one another. The density of the attachment points, placed on the supportive backing, depends on the type and ease for securing tissue to attachment points and on the distribution of loads generated by the attached tissue over each of the attachment points. Furthermore, the individual attachment points may be of varying sizes and angles depending upon the desired securing effect.

The spacing between individual points can be functional in that the number, density, and placement of points are optimized to evenly distribute the loads, e.g., shearing forces and bending moments, generated by the attached tissue layer in a brow-lift procedure. Moreover, attachment points are preferably configured to penetrate partially through the soft tissue. For instance, the sharpness of attachment points is such that they allow easy penetration through the tissue layer.

Figure 5A:
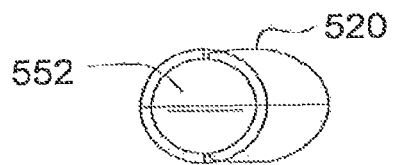
FIG. 5A shows a top view of an attachment point, according to the present invention.
Figure 5C:
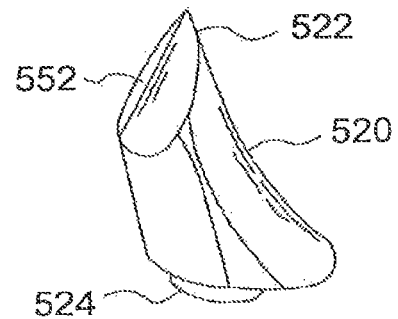
FIG. 5C shows a perspective view of the attachment point of FIG. 5A.
Figure 5B:
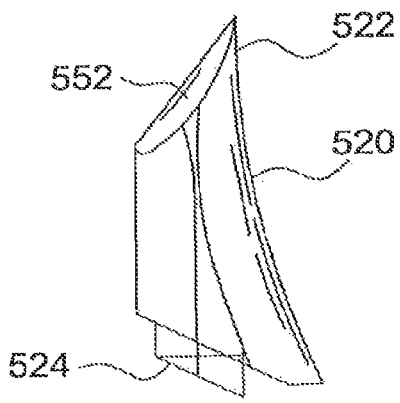
FIG. 5B shows a side view of the attachment point of FIG. 5A.
Figure 5D:
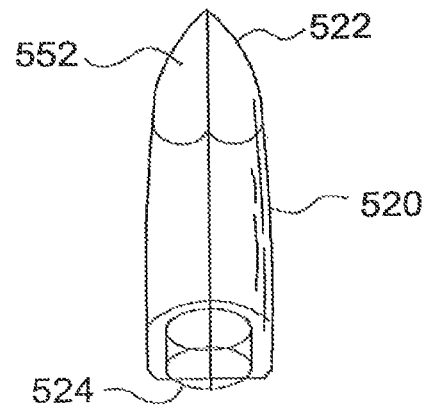
FIG. 5D shows a back view of the attachment point of FIG. 5A.

Referring to FIGS. 5A-5D, a preferred variation for an attachment point on a temporal brow lift device is shown. FIG. 5A shows a top view of a single attachment point 520 having a swept face 552. FIG. 5B is a side view of attachment point 520 comprising distal pointed end 522 and proximal base end 524. FIGS. 5C and 5D, represents represent the back view and perspective view, respectively, of the attachment point shown in FIG. 5A. Although any variations of attachment points discussed above may be used on the temporal brow lift device, this variation is preferable because it is able to readily pierce tissue through and simultaneously secure the tissue solidly by resisting any bending moments. In particular, swept face 552 can be specifically faceted so that it is preferably oriented to be essentially perpendicular to the plane of the tissue being penetrated, even though the tine axis defined by attachment point 520 may not be perpendicular to the plane of the tissue or scalp.

The attachment points 520 can be manufactured separately and attached, however, preferably the attachment points are made integral with the temporal brow lifting device. Integrating the attachment point(s) 520 with the backing not only provides uniformity in material type but also eliminates contact interfaces, which in turn may provide superior material strength and resistance to bending.

The attachment points 520 are preferably manufactured or attached so that they are all substantially erected perpendicular to the plane of the supportive backing. However, the attachment points are faceted such that the tips of attachment points 520 are effectively perpendicular to the tissue to be penetrated. Attachment points 520 may also be manufactured or assembled so that they point in different predetermined directions, depending on the desired application. Furthermore, attachment points 520 can optionally be made of varying sizes.

Figure 6A:
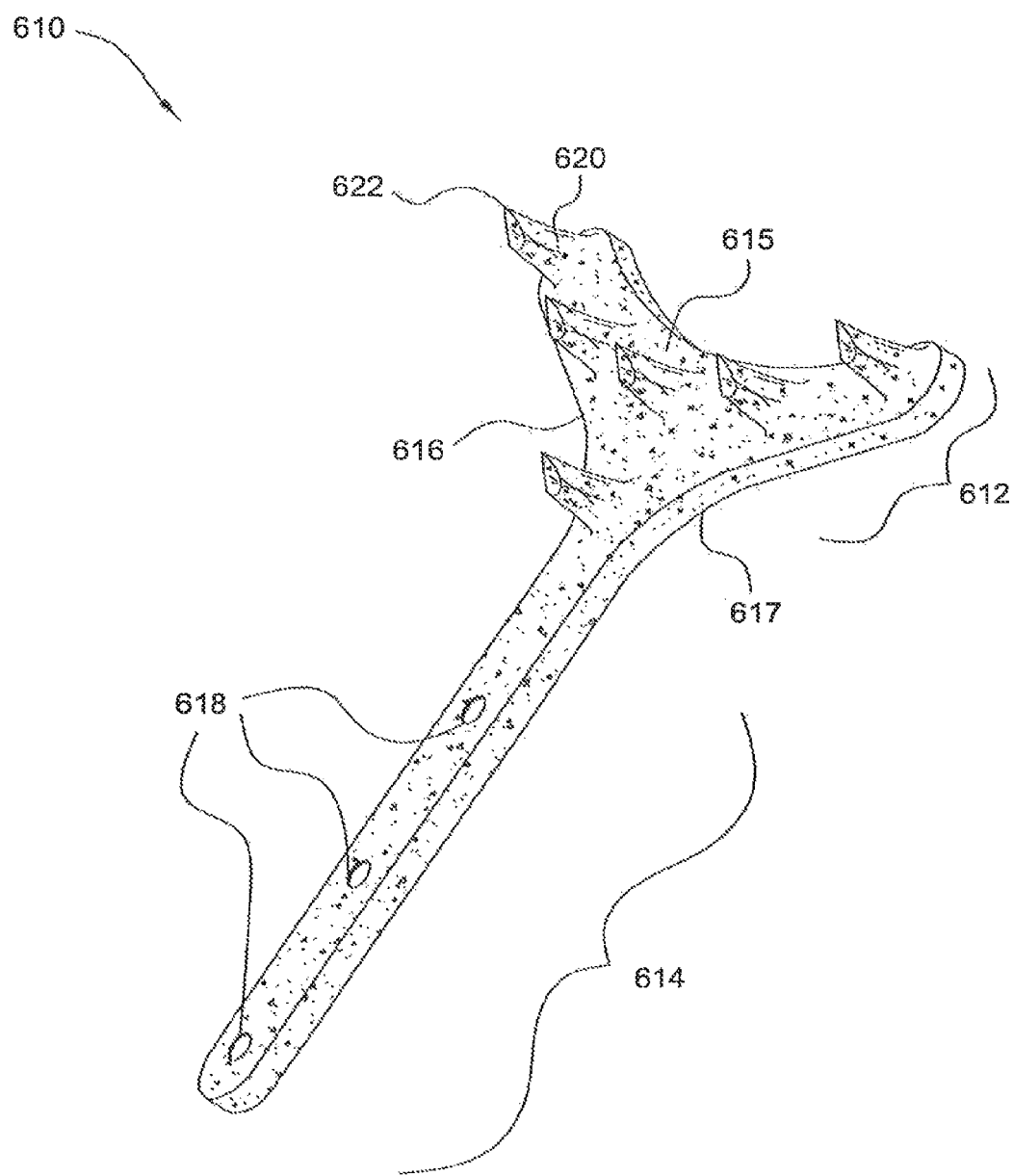
FIG. 6A shows a perspective view of a temporal brow lifting device according to an embodiment of the present invention.

Referring to FIG. 6A, a perspective view of a temporal brow lifting device according to an embodiment of the present invention is shown. The temporal brow lifting device comprises a supportive backing 616 having a shape of a curvilinear end region 612 and a tail end region 614. The supportive backing 616 is comprised of a distal surface 615 and a proximal surface 617. The distal surface 615 of the supportive backing 616 provides a platform for attaching the plurality of attachment points 620, while the proximal surface 617 provides a base for placement of the temporal brow lifting device 610 into the patient's body. The plurality of attachment points 620 distributes tension over the contact area between the temporal brow lifting device and the tissue layer. The tension or forces, generally, are also distributed in the tissue and in the supportive backing parallel to the interfaces between the tissue and the device.

Figure 6B:
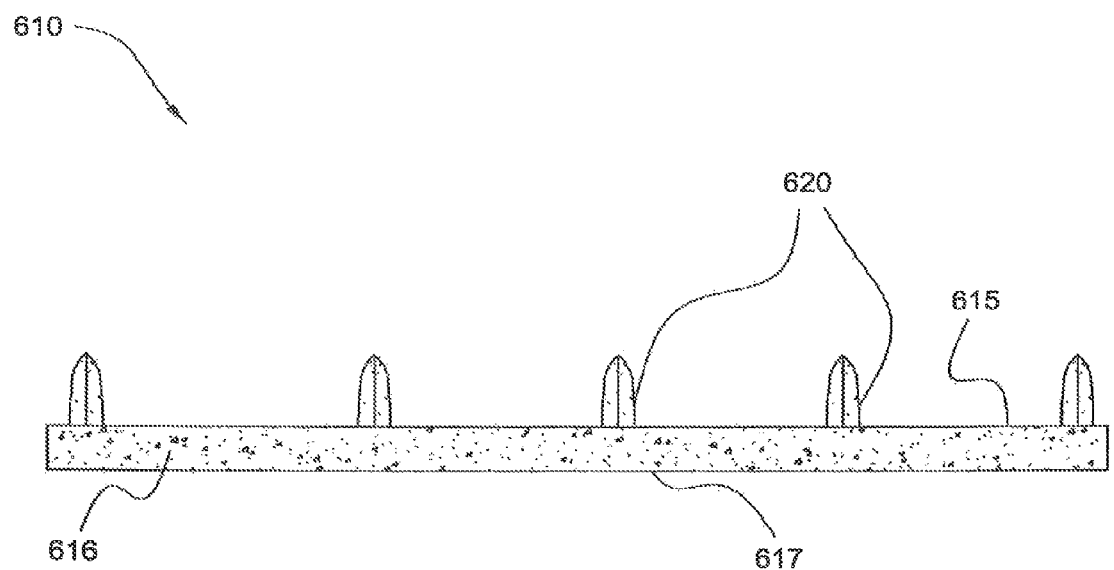
FIG. 6B shows a front view of the device of FIG. 6A.

Referring to FIG. 6B, a front view of the temporal brow lifting device 610 is shown. The plurality of the attachment points 620, also called "tines" or "prongs," are integral to the supportive backing 616. The attachment points are projecting perpendicular to the plane of the device. The plurality of the attachment points allows lifting of brows in the multi-vector direction, resulting in a smoother and uniform lifting pattern.

Figure 6C:
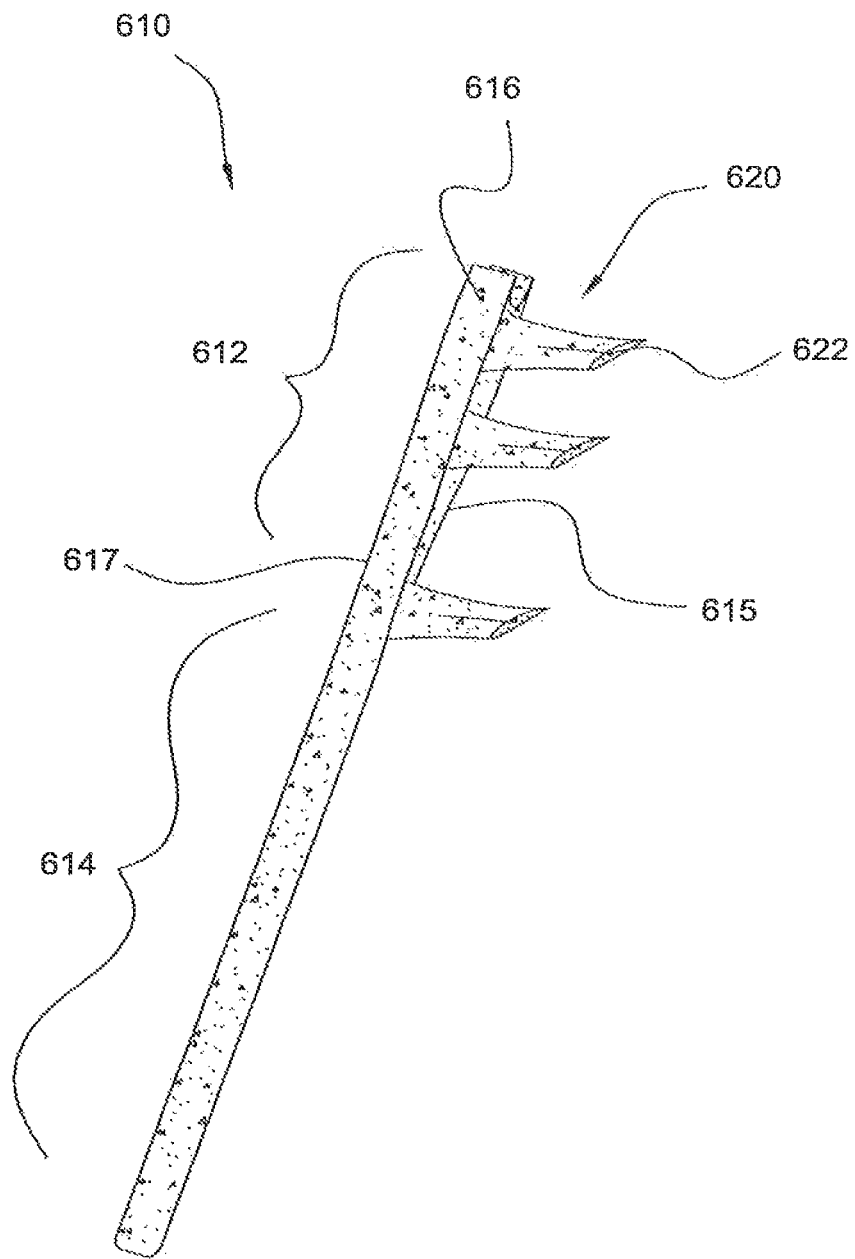
FIG. 6C is a side view of the device of FIG. 6A.

Referring to FIG. 6C, a side view of the temporal brow lifting device 610 is shown. The plurality of the attachment points 620, integral to the supportive backing 616. The attachment points are provided on the distal surface 615 of the supportive backing 616, while the proximal surface 617 is planar and devoid of an attachment point.

Figure 7A:
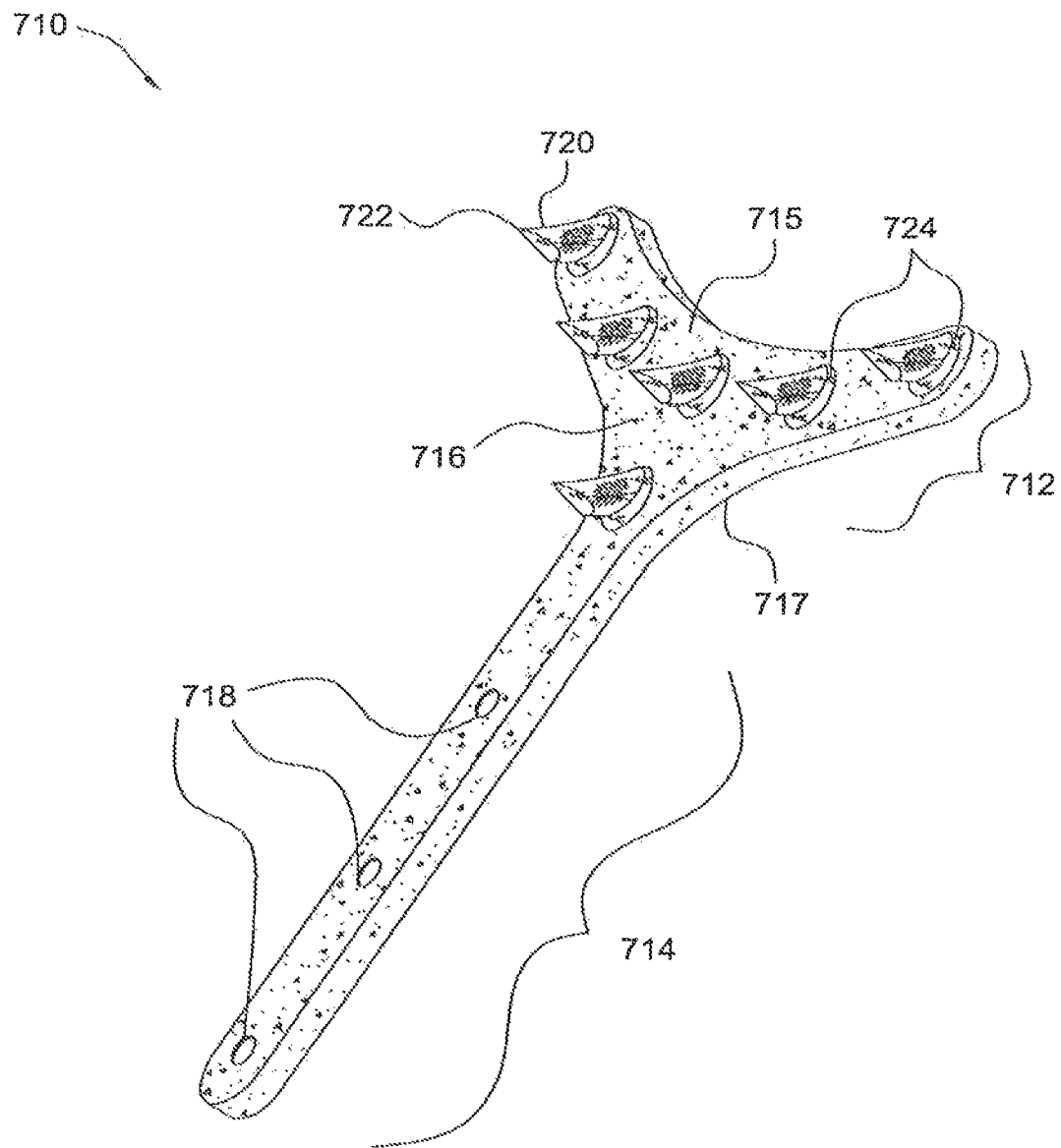
FIG. 7A shows a perspective view of a temporal brow lifting device according to another embodiment of the present invention.

Referring to FIG. 7A, a perspective view of a temporal brow lifting device, according to another embodiment of the present invention is shown. The temporal brow lifting device 710 comprises of a supportive backing 716 having a distal surface 715 and a proximal surface 717. The supportive backing 716 comprises of a curvilinear end region 712 and a tail end region 714. The curvilinear region 712 further comprises of a plurality of attachment points 720 protruding from the distal surface 715 of the supportive backing 716.

Figure 7B:
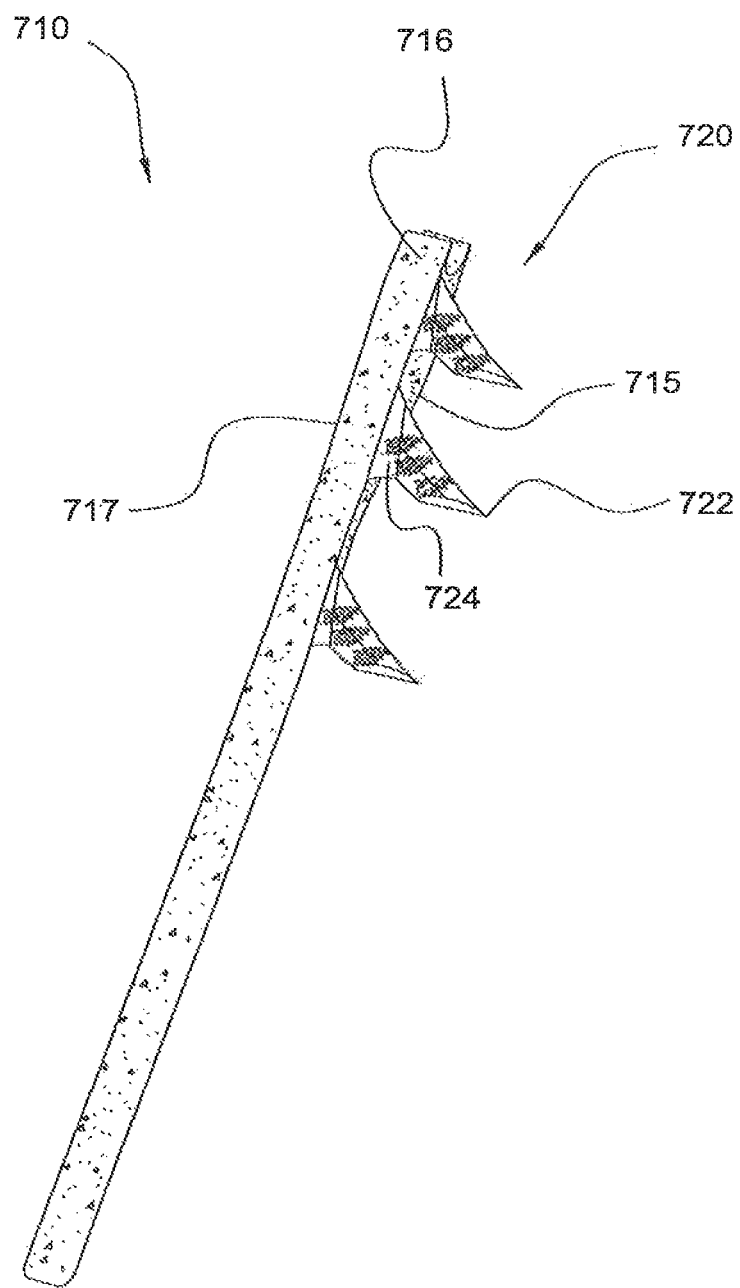
FIG. 7B represents a side view of the temporal brow lifting device of FIG. 7A.

Referring to FIG. 7B, a side view of the temporal brow lifting device 710 is shown. The attachment points are protruding at an angle elevation in parallel direction towards the tail end region. The attachment point 720 comprising a distal pointed end 722 and a proximal base end 724. The attachment point 720 of the present embodiment is manufactured separately and attached to the supportive backing 716. The attachment point 710 is affixed to the supportive backing 716 from the proximal base 724 of the attachment point.

Figure 8:
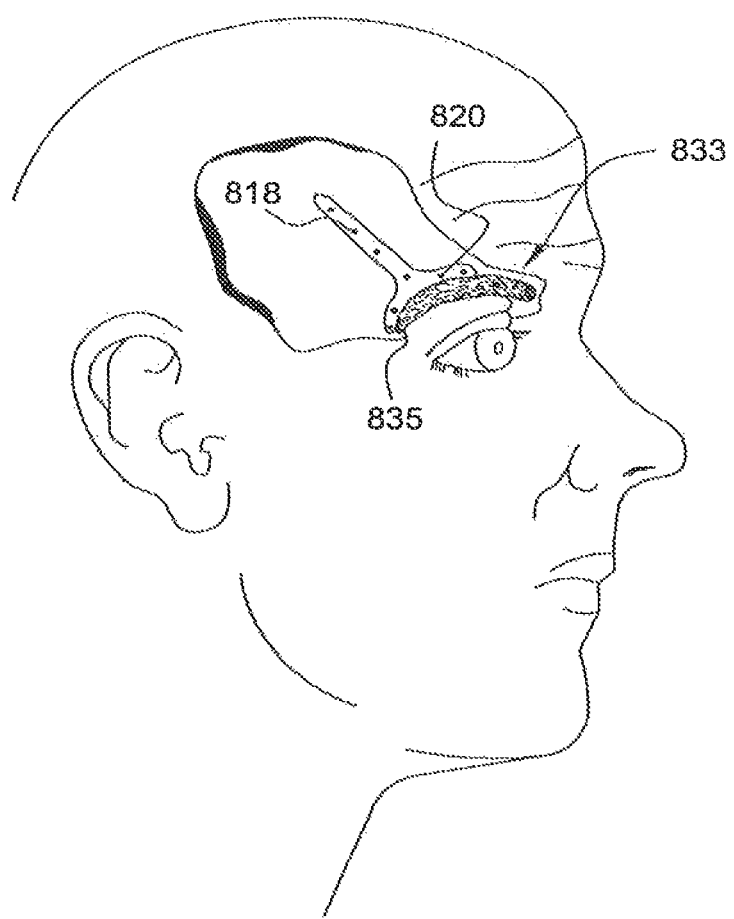
FIG. 8 is a schematic view of the temporal brow lifting device according to an embodiment of the present invention, being used in a brow-lift procedure.

Referring to FIGS. 8, a device being used for the temporal brow lifting surgical procedure, according to an embodiment of the present invention is shown. The temporal brow lifting device 810 is designed to place against the brow of the user in a low profile to provide a brow lift. The temporal brow lifting device 810 is comprises of a curvilinear end region and a tail end region. The tail region extends from the mid-portions of the device, and comprises of a plurality of cavities 818. The cavity on the tail region is used to secure device at the desired elevated position. The temporal brow lifting device 810, generally, is inserted under a patient's brow 833 while securely interlocking a small portion of the brow to the device preferably via a plurality of attachment points 820. After dissection of the lateral orbital rim of brow 835, a tissue layer of brows 837 is raised over the attachment points 820 to lift the brow. The temporal brow lifting device 810 is secured into the deep temporal fascia by suturing it through the cavities 818 of the tail region.

Various other embodiments are possible within the spirit of the invention and the aforementioned examples and embodiments are just meant to be for explanatory purposes, and in no way intend to bind the invention in any manner. The temporal brow lifting device of the present invention can be made from various kinds of materials available in the field and can be applied in brow lift surgical and similar surgical procedures known to a person skilled in the art. The invention intends to cover all the equivalent embodiments and is limited only by the appended claims.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of tissue lifting in a temporal brow-lift surgical procedure, said method comprising the steps of:
   (a) setting tissue from the temporal brow region to be approximated on a tissue lifting device, wherein the tissue includes a temporoparietal fascia layer, and wherein the tissue lifting device comprises:
      (I) a supportive backing having a proximal surface and a distal surface, said supportive backing comprising:
         (i) a proximal end that terminates in a curvilinear region, said curvilinear region defining two extensions connected by an arcuate portion, said arcuate portion being sized and configured to match a length and a curvature of a lateral orbital rim of a user; and
         (ii) a tail region extending from the curvilinear region to a distal end of the supportive backing, wherein said tail region comprises a plurality of holes through the supportive backing, between the proximal surface and the distal surface, said plurality of holes being configured to accept a suture to secure said tissue lifting device into deep temporal fascia of the user; and
      (II) a plurality of attachment points protruding from the distal surface of the curvilinear region of the supportive backing, said plurality of attachment points being configured to penetrate tissue proximal to the lateral orbital rim of the user;
   (b) mobilizing said tissue via said tissue lifting device by moving the tissue lifting device away from the eye of the user;
   (c) securing the curvilinear region of the supportive backing at the temporoparietal fascia layer at the brow region via the attachment points; and
   (d) securing the tail region of said tissue lifting device to a deep temporal fascia by suture through the plurality of holes in the tail region.

2. The method of claim 1, wherein said tissue in said step (a) is set on said tissue lifting device via said plurality of attachment points.

3. The method of claim 1, further comprising a preliminary step of cutting said tissue by a predetermined length.

4. The method of claim 3, wherein said tissue in said step (b) is mobilized by said predetermined length.

5. The method of claim 1, wherein the proximal surface has no attachment points.

6. The method of claim 1, wherein said supportive backing is formed from a bio-resorbable material.

7. The method of claim 6, wherein said bio-resorbable material comprises a polymer or copolymer.

8. The method of claim 7, wherein said polymer or copolymer comprises one or more materials selected from the group consisting of polyglycolide, polylactide, poly-alpha-caprolactone, polydiaxanone, polyglyconate, polylactide-co-glycolide, their mixtures, alloys, and random and block copolymers.

9. The method of claim 1, wherein said supportive backing comprises porous material.

10. The method of claim 9, wherein said porous material comprises a mesh, net, or lattice.

11. The method of claim 1, wherein the curvilinear region and the tail region are a single monolithic supportive backing.

12. The method of claim 1, wherein said curvilinear region has a lateral length in the range of between 50 mm and 20 mm.

13. The method of claim 1, wherein said attachment points are formed from a bio-resorbable material.

14. The method of claim 1, further comprising raising the temporoparietal fascia over the attachment points.

15. The method of claim 1, wherein securing the curvilinear region of the supportive backing comprises placing the temporoparietal fascia in contact with the curvilinear region of the supportive backing.

16. The method of claim 1, securing the curvilinear region of the supportive backing comprises positioning the device onto the lateral orbital rim of a user.

17. The method of claim 1, further comprising a preliminary step of dissecting at the lateral orbital rim of the brow.

18. The method of claim 17, wherein said dissecting the lateral orbital rim comprises cutting said tissue by a predetermined length.

* * * * *